(12) United States Patent
Alby

(10) Patent No.: US 6,241,730 B1
(45) Date of Patent: Jun. 5, 2001

(54) INTERVERTEBRAL LINK DEVICE CAPABLE OF AXIAL AND ANGULAR DISPLACEMENT

(75) Inventor: Albert Alby, Paris (FR)

(73) Assignee: Scient'x (Societe a Responsabilite Limitee) (FR)

( * ) Notice: Subject to any disclaimer, the term of this patent is extended or adjusted under 35 U.S.C. 154(b) by 0 days.

(21) Appl. No.: 09/200,730

(22) Filed: Nov. 27, 1998

(30) Foreign Application Priority Data

Nov. 26, 1997 (FR) .................................................. 97 14831

(51) Int. Cl.⁷ ...................................................... A61B 17/56

(52) U.S. Cl. ................................ 606/61; 606/72; 606/73; 403/120

(58) Field of Search ................................. 606/61, 73, 72; 623/17.11; 403/120, 121

(56) References Cited

U.S. PATENT DOCUMENTS 5,375,823 * 12/1994 Navas ...................................... 606/61
5,529,420 * 6/1996 Henkel et al. ........................ 403/120

\* cited by examiner

*Primary Examiner*—Henry J. Recla
*Assistant Examiner*—Julian W. Woo
(74) *Attorney, Agent, or Firm*—Bacon & Thomas PLLC

(57) ABSTRACT

An intervertebral link device including at least one damper element constituted by a cage and a pin designed to be connected to bone anchor elements. The pin being engaged in a housing of the cage and being fitted with two elastically deformable members operating in opposition to an applied traction force or compression force. The damper element includes a pin that is mounted inside the cage by a joint allowing multidirectional relative pivoting between the pin and the cage, at least about the axes contained in a plane perpendicular to the pin and angular abutment between the cage and the pin enabling the multidirectional relative pivoting to be limited in amplitude to a determined value of about 4°.

8 Claims, 2 Drawing Sheets

INTERVERTEBRAL LINK DEVICE CAPABLE OF AXIAL AND ANGULAR DISPLACEMENT

BACKGROUND OF THE INVENTION

1. Field of the Invention

The present invention relates to an intervertebral link device intended, in particular, for treatment of defects or pathological states of the vertebral column or of the vertebrae.

More particularly, the invention relates to an intervertebral stabilization device designed to hold at least two vertebrae in an appropriate relative position, e.g. for the purpose of correcting a patient's compacting of the vertebrae, scoliosis, lordosis, kyphosis, or intervertebral instability.

The invention can also be applied in the field of bone or joint links performed internally or externally.

2. Description of the Related Art

In the field of the preferred application to osteosynthesis of the spinal column, there exist numerous systems made up of link elements that are applied to the posterior face of the vertebrae and are fixed by screws implanted in the vertebral pedicles.

That type of assembly makes it possible to secure a plurality of vertebrae to one another, so as to obtain arthrodesis or bone fusion.

In the above technical field, a first category of devices is known comprising at least two link plates provided with slots and disposed longitudinally on either side of the spinous processes, and at least four fixing screws disposed in pairs on the pedicles on either side of two successive vertebrae. The threaded free ends of said screws pass through the slots in said plates and final fixing of the plates is provided, after adjustment, by nuts screwed onto the threaded ends.

The main advantage of such link plates lies in their rigidity. Nevertheless, it often happens that such rigidity can also constitute a drawback since it does not allow the surgeon to adapt the plates to the morphology of the vertebrae of a particular patient.

A second category of intervertebral link devices is also known, made up of a circular section rod fixed to bone anchor screws. An advantage of link rods lies in the fact that their circular section having a diameter lying in the range 4 mm to 7 mm makes it possible for the surgeon to shape them as required by using appropriate bending tools.

Nevertheless, it appears that an intervertebral stabilization device, whether of the plate type or of the rod type, once implemented, constitutes a system that is rigid, thereby applying mechanical stresses to the intervertebral joints adjacent to the joint being stabilized.

To remedy that problem, document EP 0 516 567 proposes an intervertebral stabilization device made in the form of a damper suitable for elastically withstanding axial compression and elongation. Such a stabilization device is capable of damping movement both in compression and in extension, thereby allowing the facets of the vertebrae to move asymmetrically relative to one another. Nevertheless, it turns out that such an intervertebral stabilization device designed to damp compression and extension movements does not give entire satisfaction.

It turns out to be necessary to have an intervertebral stabilization device that is suitable not only for damping axial movements in compression and traction, but also for damping lateral bending movements and bending and stretching movements in the antero-posterior plane.

Attempts have also been made to adapt the extent to which the mobility of the vertebrae to be stabilized is reduced as a function of each particular case, so as to leave a determined amount of lateral bending possible and a certain amount of axial compression and traction, the small amount of mobility that is allowed being predetermined to take up major stresses while still allowing micromovements to take place which are believed to favor bone fusion.

SUMMARY OF THE INVENTION

The object of the invention is to satisfy this need by proposing an intervertebral link device designed to damp axial compression and traction movements, and also lateral bending movements and bending and stretching movements in the antero-posterior plane.

Another object of the invention is to propose an intervertebral stabilization device adapted to allow micromovements so as to ensure bone fusion.

Another object of the invention is to propose an intervertebral link device capable of axial and angular displacement and that is highly reliable in operation.

To achieve the various objects above, the invention provides an intervertebral link device comprising at least one damper element constituted by a cage and a pin designed to be connected to bone anchor elements, the pin being engaged in a housing of the cage and being fitted with two elastically deformable members operating in opposition to an applied traction force or compression force.

According to the invention, the damper element comprises:

a pin which is mounted inside the cage by a joint allowing multidirectional relative pivoting between the pin and the cage at least about axes contained in a plane perpendicular to the pin; and angular abutment between the cage and the pin, enabling the multidirectional relative pivoting to be limited in amplitude to a determined value of about 4°.

BRIEF DESCRIPTION OF THE DRAWINGS

Various other characteristics appear from the following description made with reference to the accompanying drawings which show non-limiting examples of embodiments of the invention.

DETAILED DESCRIPTION OF THE PREFERRED EMBODIMENTS

The invention provides a device 1 for linking together at least two vertebrae and designed to be connected to implants or to bone anchor elements of the pedicular screw type. In the example shown in FIGS. 1 to 3, the implants (not shown)

are interconnected by a link rod 4 constituted by at least two rigid segments 4A and 4B which are interconnected by means of a damper element 7 interposed between their facing free ends, so as to oppose elastic resistance between the segments 4A and 4B with amplitude that is controlled not only in axial compression and traction a, but also in angular bending b.

Naturally, a single link rod 4 may include a plurality of dampers 7 disposed between the vertebrae. Also, the link rod 4 may advantageously be cut to a selected length and curved to a selected radius.

Figure 1:
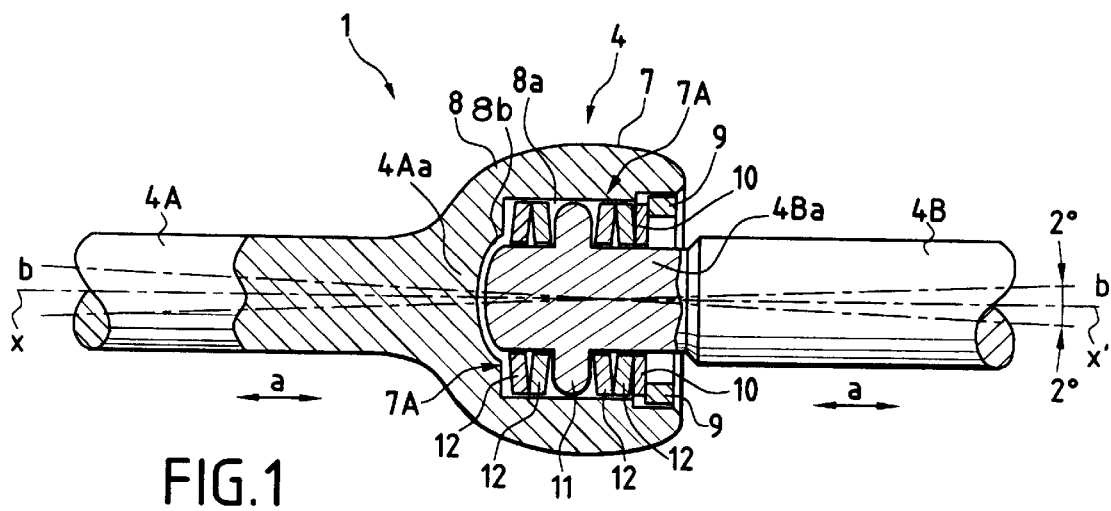
FIG. 1 is a longitudinal section view of an intervertebral link element including an interposed damper of the invention.
Figure 2:
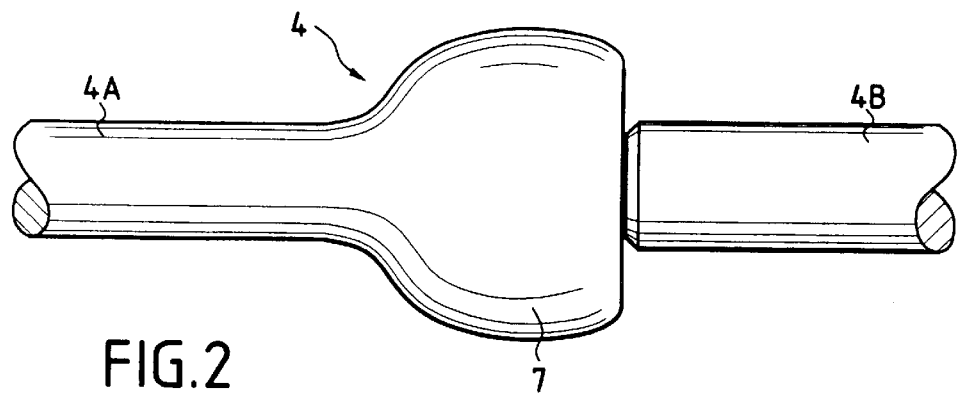
FIG. 2 is a plan view of FIG. 1.

As can be seen more clearly in FIG. 1, the damper element 7 is made up of two elastically deformable members 7A disposed around the free end of a pin 4Ba extending one of the segments 4B constituting the rod 4. The pin 4Ba is engaged inside a housing 8a formed in a blind sleeve or cage 8 made at the free end 4Aa of the other link segment 4A. In the embodiment shown in FIG. 1, the damper element 7 comprises a rigid piston 11 formed on the pin 4Ba to constitute a joint 11 making multidirectional relative pivoting possible between the cage 8 and the pin 4Ba, at least about axes contained in a plane perpendicular to the longitudinal axis x-x' of the damper element 7 when the pin and the cage are in alignment.

In a preferred embodiment, the resulting joint 11 is of the ball-and-socket type that also allows the cage to rotate relative to the pin about the axis x-x'. The joint 11 is constituted by a collar projecting radially from the pin 4Ba and having and outside surface with a rounded profile that is designed to come into contact with the inside surface of the housing 8a in the cage 8. In the example shown in FIG. 1, the collar 11 is an integral part of the pin 4Ba, while in the example shown in FIG. 4, the collar 11 is constituted by a separate ring that is fixed on the pin 4Ba.

The collar 11 is disposed relative to the pin 4Ba in such a manner as to receive thrust on both of its lateral faces from two sets of spring washers 12 each in the form of a pair of facing frustoconical cups of identical diameter stacked on the pin 4Ba. The washers 12 and the joint 11 occupy at least part of the circular section housing 8a whose end wall constitutes a compression abutment for one of the elastically deformable members 7A. It should be observed that the spring washers 12, which are also known as "Belleville" washers, can be replaced by elastomer rings.

According to another characteristic of the invention, the housing 8a of the cage 8 is closed by a first washer 9 secured to the cage 8 and having an inside face against which there bears a second washer 10 secured to the pin 4Ba. The deformable members 7A are placed freely on the pin 4Ba between the washer 10 and the end wall of the housing 8a. For example, the first washer 9 which constitutes an axial abutment can be implemented in the form of a threaded ring screwed into tapping made inside the housing from its outer end, thereby making it possible to adjust the extension position of the damper. It should be observed that the second washer 10 which is secured to the pin 4Ba constitutes a bearing surface for an elastically deformable member 7A. This second washer 10 serves as an abutment for the damper in axial traction. This second washer 10 thus makes it possible to exert compression force on the deformable member without damaging it. In addition, according to an advantageous characteristic, the second washer 10 can be made of a material that is identical to that constituting the elastically deformable member, so as to make it possible to control the friction which appears between the second washer 10 and the elastically deformable member 7A.

The elastically deformable members 7A are maintained with axial clearance that makes it possible, when they deform elastically, to accommodate relative axial movements in compression and traction between the pin 4Ba and the cage 8. For example, it is possible to obtain axial compression or traction having a value a=±8 mm. In addition, the elastically deformable members 7A are mounted so as to allow multidirectional relative pivoting between the pin 4Ba and the cage 8. In this respect, the washers are mounted inside the housing 8a with clearance relative to the inside wall of the housing.

According to an advantageous characteristic of the invention, the damper element 7 includes an angular abutment for limiting the multidirectional relative pivoting to a determined value having an amplitude of about 4°. Thus, as can be seen more clearly in FIG. 1, the displacement b of the pin 4Ba in the cage 8 relative to its normal, aligned position is ±2°. In the example shown, the angular abutment is constituted by the housing 8a against which the pin 4Ba comes into abutment, which pin has a predetermined amount of radial clearance relative to the housing 8a to enable relative pivoting to take place through the predetermined angle b. Thus, the pin 4Ba presents radial clearance both between its collar 11 and the housing 8a, and between its free end and a blind recess 8b extending the housing 8a. Relative pivoting between the cage 8 and the pin 4Ba is thus limited by implementing two angular abutments defined by the co-operation firstly between the collar 11 and the housing 8a, and secondly between the free end of the pin and the blind recess 8b. It should be observed that the two abutments constituted in this way are set up in opposition about the axis x-x'. This allows limited bending to be obtained between the cage and the pin in all directions of angular displacement.

Figure 3:
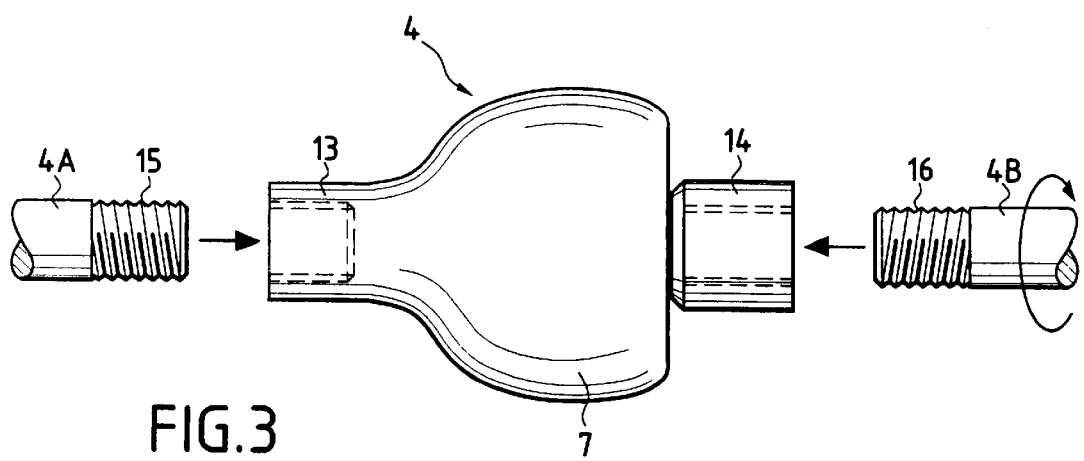
FIG. 3 shows a link element fitted with a variant interposed damper of the invention.

In a variant embodiment shown in FIG. 3, the damper element 7 is an independent element having axial end zones 13 and 14 designed for screw connection with the corresponding ends 15 and 16 of respective segments 4A and 4B of a link rod 4. Naturally, the segments can be of various lengths selected from a range as a function of the case being treated. For example, the ends of the segments 4A and 4B of the link rod 4 can be threaded so as to be suitable for screwing into tapped holes formed in the axial end portions 13 and 14 of the damper element 7. When a rod 4 is to be made that has a plurality of dampers, use will be made of segments of predetermined lengths that are threaded at both ends.

Figure 4:
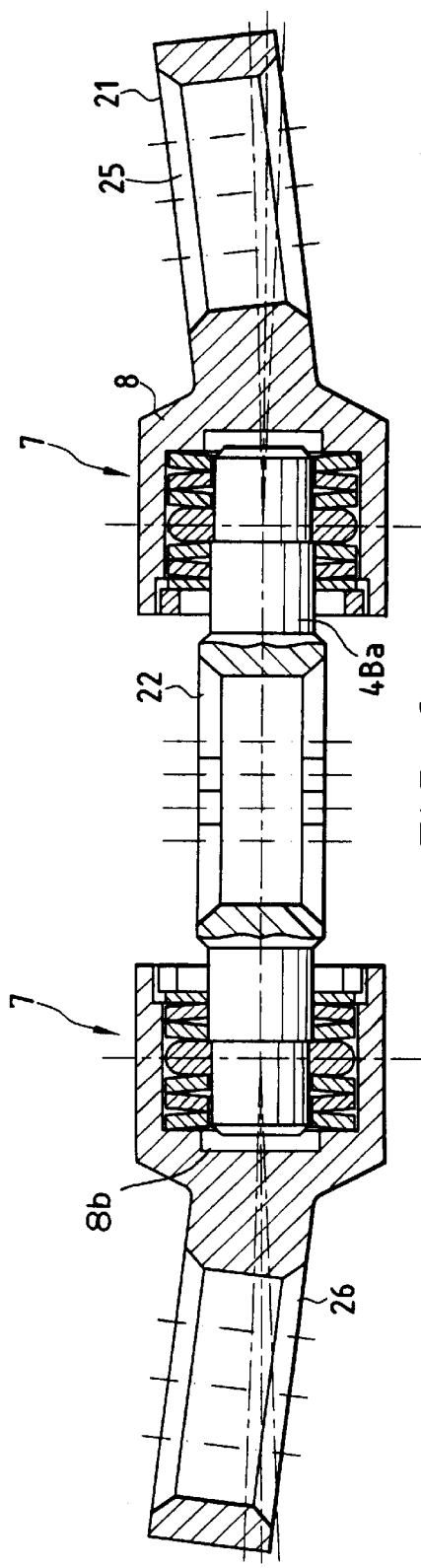
FIG. 4 is a section view showing another variant embodiment of a link element fitted with an interposed damper of the invention.
Figure 5:
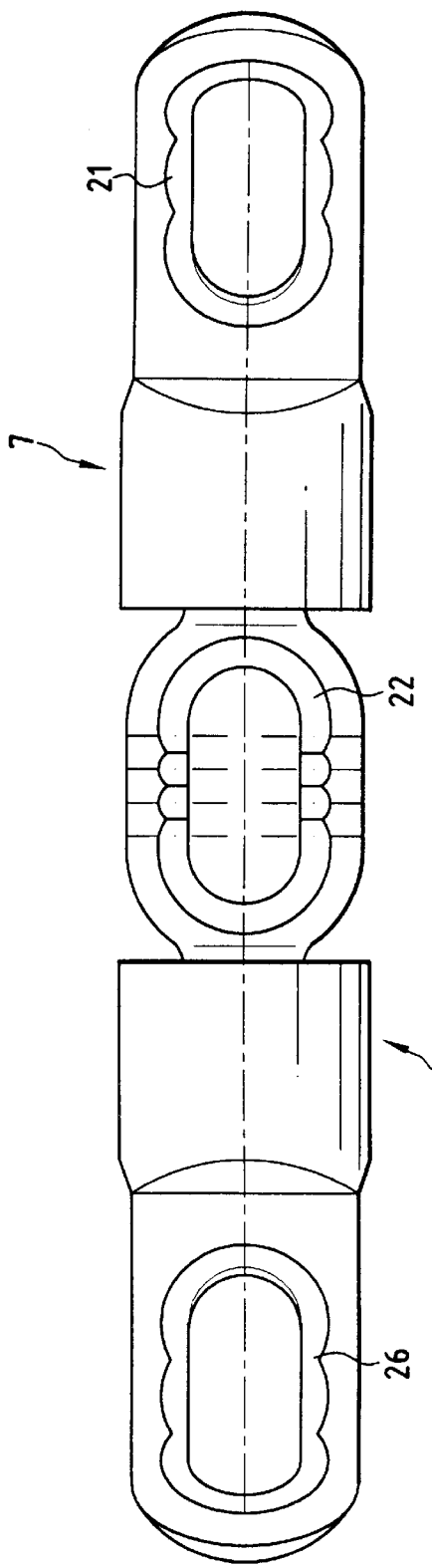
FIG. 5 is a plan view of the link element shown in FIG. 4.

The above-described damper element 7 can be adapted to a link element other than an element of the rod type. To this end, FIGS. 4 and 5 show another embodiment in which a damper element 7 is designed to be associated with plates of rectangular section. In the example shown, the intervertebral link device 1 comprises a damper element 7 whose cage 8 is extended by a first plate 21, while its pin 4Ba is extended by a second plate 22 of generally rectangular section. The plates 21 and 22 conventionally include axial passages 25 for bone implants.

In the example shown in FIG. 4, the intervertebral link device 1 has a second damper element 7 whose pin 4Ba is connected to the second link plate 22, while its cage 8 is extended by a third plate 26.

The invention is not limited to the examples described and shown, and numerous modifications can be made thereto without going beyond its ambit.

The present invention is by no means restricted to the above-described preferred embodiments, but covers all variations that might be implemented by using equivalent functional elements or devices that would be apparent to a person skilled in the art, or modifications that fall within the spirit and scope of the appended claims.

What is claimed is:

1. An intervertebral link device comprising at least one damper element comprising a cage and a pin having a collar, a free end and a securable end, the securable end of the pin designed to be connected to bone anchor elements, the free end of the pin being engaged in a housing of the cage and being fitted with two elastically deformable members operating in opposition to an applied traction force or compression force, wherein the damper element comprises:

the pin which is mounted inside the cage by a joint allowing multidirectional relative pivoting between the pin and the cage at least about axes contained in a plane perpendicular to the pin; and an angular abutment device having a first angular abutment between the housing and the collar of the pin, enabling the multidirectional relative pivoting to be limited in amplitude to a determined value of about 4°, the angular abutment device further comprising a second angular abutment at the free end of the pin and the housing against which the free end of pin comes into abutment, the pin and the housing having predetermined radial clearance to allow relative pivoting of the determined value.

2. The device accord according to claim 1, wherein the damper element has radial clearance firstly between the joint and the housing, and secondly between the free end of the pin and a blind recess extending inside the housing.

3. The device according to claim 1, wherein the damper element comprises the two elastically deformable members disposed around the pin on either side of the joint, the elastically deformable members being mounted inside the cage and being retained with predetermined axial and angular clearance, relative movement between the cage and the pin being obtained by elastically deforming the deformable members and by the predetermined clearance.

4. The device according to claim 1, wherein the joint comprises a collar, the collar having lateral faces and carried by the pin and receiving thrust on each of its lateral faces from two sets of washers forming pairs of opposite facing frustoconical cups of identical diameter disposed on the pin on either side of the collar so that the washers and the joint occupy the annular space defined between the pin and the inside wall of the cage.

5. The device according to claim 4, wherein the elastically deformable members are retained by a washer fixed to the pin and bearing against an axial abutment carried by the cage.

6. The device according to claim 1, wherein the damper element is an independent element having coupling portions at its axial ends designed for coupling to corresponding end portions of link elements.

7. The device according to claim 6, wherein the coupling portions respectively of the damper element and of the end portions of the link elements comprise threaded portions.

8. The device according to claim 1, wherein the damper element comprises the pin extended by a link element, and the cage extended by a link element.

* * * * *